(12) United States Patent
O'Connor et al.

(10) Patent No.: US 9,872,820 B2
(45) Date of Patent: *Jan. 23, 2018

(54) PERSONAL CARE SENSORY AGENTS

(71) Applicants: Dow Global Technologies LLC, Midland, MI (US); Rohm and Haas Company, Philadelphia, PA (US)

(72) Inventors: Ying O'Connor, Coatesville, PA (US); Curtis Schwartz, Ambler, PA (US); Qichun Wan, Midland, MI (US); Thomas H. Peterson, Midland, MI (US); Thomas P. Clark, Midland, MI (US); John W. Kramer, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/430,079

(22) PCT Filed: Sep. 18, 2013

(86) PCT No.: PCT/US2013/060281
§ 371 (c)(1),
(2) Date: Mar. 20, 2015

(87) PCT Pub. No.: WO2014/047102
PCT Pub. Date: Mar. 27, 2014

(65) Prior Publication Data
US 2015/0224038 A1   Aug. 13, 2015

Related U.S. Application Data

(60) Provisional application No. 61/704,663, filed on Sep. 24, 2012.

(51) Int. Cl.
| | | |
|---|---|---|
| C08F 210/00 | (2006.01) | |
| C08F 210/02 | (2006.01) | |
| C08F 210/14 | (2006.01) | |
| C08F 210/16 | (2006.01) | |
| A61K 8/31 | (2006.01) | |
| A61Q 11/00 | (2006.01) | |
| A61K 8/81 | (2006.01) | |
| A61K 8/04 | (2006.01) | |
| A61Q 19/00 | (2006.01) | |

(52) U.S. Cl.
CPC ............... *A61K 8/31* (2013.01); *A61K 8/042* (2013.01); *A61K 8/8111* (2013.01); *A61Q 11/00* (2013.01); *A61Q 19/00* (2013.01); *A61K 2800/30* (2013.01)

(58) Field of Classification Search
CPC ........ C08F 210/00; C08F 4/64; C08F 210/02; C08F 210/14; C08F 210/16
See application file for complete search history.

(56) References Cited

U.S. PATENT DOCUMENTS

| | | | |
|---|---|---|---|
| 4,701,432 A | 10/1987 | Welborn, Jr. | |
| 5,272,236 A | 12/1993 | Lai et al. | |
| 5,322,728 A | 6/1994 | Davey et al. | |
| 6,180,123 B1 | 1/2001 | Mondet | |
| 6,525,157 B2 | 2/2003 | Cozewith et al. | |
| 6,869,599 B2 | 3/2005 | Tournilhac et al. | |
| 6,960,635 B2 | 11/2005 | Stevens et al. | |
| 2007/0031361 A1* | 2/2007 | Herrmann | A61K 8/8111 424/70.11 |
| 2007/0295465 A1* | 12/2007 | Dyer | A47K 10/16 162/111 |
| 2011/0064683 A1 | 3/2011 | Jordan et al. | |
| 2015/0224038 A1 | 8/2015 | O'Connor et al. | |

FOREIGN PATENT DOCUMENTS

| | | | | |
|---|---|---|---|---|
| JP | 10316787 A | * | 12/1998 | |
| JP | 2008189603 A | | 8/2008 | |
| JP | 2009029271 A | | 2/2009 | |
| WO | 97/32946 A1 | | 9/1997 | |
| WO | WO 9732946 A1 | * | 9/1997 | ............. A61K 8/042 |
| WO | WO 2011022523 A2 | * | 2/2011 | ............ C09J 123/02 |
| WO | 2014047102 A2 | | 3/2014 | |

OTHER PUBLICATIONS

Yalvac et al., High Flow Affinity GA POE-based Hot Melt Adhesives. Dow Elastomers. Published Jul. 2013.*

* cited by examiner

*Primary Examiner* — Timothy Thomas
*Assistant Examiner* — George W Kosturko
(74) *Attorney, Agent, or Firm* — Edward L. Brant

(57) ABSTRACT

Described are personal care, preferably skin care compositions, comprising polyolefin blends comprising at least one metallocene catalyzed polyolefin with a density above 0.90 g/cm$^3$, at least one metallocene catalyzed polyolefin with a density equal to or below 0.90 g/cm$^3$, provided that the average melt index for the polyolefin blend is greater than 7; and a cosmetically acceptable hydrocarbon oil, provided that the composition does not contain ethylene acrylic copolymer.

8 Claims, No Drawings

PERSONAL CARE SENSORY AGENTS

CROSS-REFERENCE TO RELATED APPLICATION(S)

This application claims priority to and is a 371 U.S.C. § 371 national phase application of International Application No. PCT/US/2013/060281, filed on Sep. 18, 2013, which claims the priority benefit of U.S. Provisional Application No. 61/704,663, filed on Sep. 24, 2012, each of which is incorporated herein by reference.

FIELD

The presently described invention is in the field of personal care.

BACKGROUND

Personal care products, particularly leave-on skin care products, require a smooth and silky feel on skin to please consumers. In fact, aesthetics are one of the most important factors in consumer satisfaction. Accordingly, the skin care art has developed sensory agents, such as silicone oils, hard particles (such as Poly(methyl methacrylate) (PMMA) particles and polyethylene (PE) particles), and silicone elastomer gels in order to impart good aesthetics. However, each of the foregoing is associated with certain drawbacks, like insufficient sensory performance, dry after-feel on skin, or relatively high cost.

Accordingly, what is needed are cost-effective high performance sensory agents, preferably with good stability and texture in skin care formulations.

DETAILED DESCRIPTION

In one embodiment, the present invention provides personal care, preferably skin care compositions, comprising polyolefin blends comprising at least one metallocene catalyzed polyolefin with a density above 0.90 g/cm$^3$, at least one metallocene catalyzed polyolefin with a density equal to or below 0.90 g/cm$^3$, provided that the average melt index for the polyolefin blend is greater than 7, preferably greater than 8; and a cosmetically acceptable hydrocarbon oil, provided that the composition does not contain ethylene acrylic copolymer.

In one embodiment, the hydrocarbon oil is selected from various carbon chain length oils, such as those sold under the tradenames LILAC, GEMSEAL 25, GEMSEAL 40, PERMETHYL 101A, PERMETHYL 99A, SILKFLO 364 NF, SILKFLO 366 NF, FANCOL POLYISO 200-CG, FANCOL POLYISO 300-CG, FANCOL POLYISO 450-CG, FANCOL POLYISO 800-CG, PANALANE L-14E, PURESYN 2, PURESYN 4, OR RITADECENE 20. In one embodiment, the hydrocarbon oil is a C14-C22 hydrocarbon oil. In one embodiment, the hydrocarbon oil is a <C14 hydrocarbon oil. In one embodiment, the hydrocarbon oil is a >C22 hydrocarbon oil.

"Personal care" relates to compositions to be topically applied to a person (including mouth, ear, and nasal cavities, but not ingested). Examples of personal care compositions include skin care products (e.g., facial lotions/creams, moisturizers, face/eye/body serums, leave on and rinse off body/hand lotions/creams, eye lotions/creams, sunscreens, foundation, blush, eye-shadow, primer, mascara, eye-liner, lipstick, cleansers, antiperspirants, deodorants, and the like) and hair care products (including shampoos, leave on and rinse off conditioners, styling gels and hairsprays). Preferably, the personal care composition is a skin care composition. Preferably, skin care composition is a leave-on skin care composition.

"Cosmetically acceptable" refers to ingredients typically used in personal care compositions, and is intended to underscore that materials that are toxic when present in the amounts typically found in personal care compositions are not contemplated as part of the present invention.

"Metallocene catalyzed polyolefins" are polyolefins produced with a metallocene catalyst as described in U.S. Pat. Nos. 4,701,432, 5,322,728, and 5,272,236, each of which is incorporated herein by reference in its entirety. As a specific embodiment of the present invention, the metallocene catalyzed polyolefins are polyethylenes produced with a metallocene catalyst. Such metallocene catalyzed polyethylenes are available e.g. from The Dow Chemical Company under the trademark AFFINITY or ENGAGE (ethylene/octene copolymers) and from Exxon Chemical Company under the trademark EXACT (ethylene/butene copolymers, ethylene/hexene copolymers, or ethylene/butene/hexene terpolymers). In one embodiment, the metallocene catalyzed polyolefin is at least one of ethylene/octene copolymers, ethylene/butene copolymers, ethylene/hexene copolymers, ethylene/propylene or ethylene/butene/hexene terpolymers, preferably an ethylene octene copolymer. In another embodiment, the metallocene catalyzed polyolefin is a propylene/alpha-olefin copolymer, which is further described in details in the U.S. Pat. Nos. 6,960,635 and 6,525,157, each of which is incorporated herein by reference in its entirety. Such propylene/alpha-olefin copolymers are commercially available from The Dow Chemical Company, under the tradename VERSIFY™, or from ExxonMobil Chemical Company, under the tradename VISTAMAXX™. Other desirable polyolefins are sold by The Dow Chemical Company under the trademarks AMPLITY, ATTANE, INFUSE, NORDEL, and VLDPE.

Without wishing to be bound by theory, we have discovered that metallocene catalyzed polyolefins of medium or high density (above 0.90 g/cm$^3$) contribute good aesthetics, but form unstable gels. Low density metallocene catalyzed polyolefins (0.86-0.90 g/cm$^3$) form stable gels, though the aesthetics are poor. Density is measured by ASTM D 792. Moreover, low molecular weight metallocene catalyzed polyolefins (Melt Index ≥8 by ASTM D 1238) showed much better solubility in a hydrocarbon medium and maintain phase homogeneity. High molecular weight metallocene catalyzed polyolefins (Melt Index <8 by ASTM D 1238) led to hard gels that are not easily workable in personal care formulations.

In one embodiment, the average melt index for the polyolefin blend is greater than 8. In one embodiment, the average melt index for the polyolefin blend is greater than 8.5.

Table 1 contains a list of commercially available metallocene catalyzed polyethylenes with their properties.

TABLE 1

| Polyolefin Name | Melt Index | Density |
| --- | --- | --- |
| AFFINITY GA 1950 | 500 | 0.874 |
| AFFINITY PL1840G | 1 | 0.909 |
| AMPLIFY EA 103 | 21 | 0.930 |
| AMPLIFY GR 202 | 8 | 0.930 |
| ATTANE 4203 | 0.8 | 0.905 |
| ATTANE 4404G | 4 | 0.904 |
| ENGAGE 8100 | 1 | 0.870 |

TABLE 1-continued

| Polyolefin Name | Melt Index | Density |
| --- | --- | --- |
| ENGAGE 8130 | 13 | 0.863 |
| ENGAGE 8200 | 5 | 0.870 |
| ENGAGE 8402 | 30 | 0.902 |
| LDPE 4016 | 16 | 0.916 |
| LDPE 640I | 2 | 0.920 |
| LDPE 955I | 35 | 0.923 |
| VERSIFY 2200 | 2 | 0.876 |
| VERSIFY 3200 | 8 | 0.876 |
| VERSIFY 4200 | 25 | 0.876 |

It is a critical feature that the composition does not contain ethylene acrylic copolymer. Copolymerizing ethylene with acrylic acid yields ethylene-acrylic acid (EAA) copolymers, which are known for use in personal care compositions. However, in the presently described skin care compositions, with their concurrent relatively low pH and low surfactant levels, EAA would deleteriously flocculate and ruin the stability of the formulation.

In one embodiment, the at least one metallocene catalyzed polyolefin with a density above 0.90 g/cm$^3$ is present in a range from 1 wt % to 60 wt % of solids by weight of the Polyolefin and Oil blend. In one embodiment, the at least one metallocene catalyzed polyolefin with a density equal to or below 0.90 g/cm$^3$ is present in a range from 1 wt % to 60 wt % of solids by weight of the Polyolefin and Oil blend. In one embodiment, the ratio of at least one metallocene catalyzed polyolefin with a density above 0.90 g/cm$^3$ to the at least one metallocene catalyzed polyolefin with a density equal to or below 0.90 g/cm$^3$ is between 1:95 and 95:1, and preferably is 1:1, 1.5:1, 2:1, 3:1.

The polyolefin blend is prepared by shearing the above-described polyolefins in a carrier fluid such as, but not limited to, aromatic hydrocarbons, aliphatic hydrocarbons, alcohols, esters, ethers, glycols, carbonates, silicones, glycol ethers at high temperature, above 100° C., preferably from 120° C. to 150° C.

In one embodiment, the polyolefin blend is referred to as an "oil gel," however, the polyolefin blend can be powder, pellet/bead, oil gel/oil paste, or water dispersion.

In one embodiment, the polyolefin blend may work together with other skin care ingredients to give a synergic effect, such as emollients (hydrocarbon oils, esters, natural oils, silicones, etc.), waxes, sensory modifiers, rheology modifiers, humectants (glycerin, etc.), sunscreen actives, natural ingredients, bio-actives, colorants, hard particles, conditioning agent, and other silicones.

EXAMPLES

Example 1

Polyolefin blends of the present invention are described in TABLE 2:

TABLE 2

|  | Batch A | Batch B |
| --- | --- | --- |
| AFFINITY GA 1950 | 6.25% | 4.17% |
| AFFINITY PL 1840 G | 6.25% | — |
| LDPE 955I | — | 4.17% |
| ATTANE 4404G | — | 4.17% |
| LILAC oil | 87.5 | 87.5 |

6.25 grams Affinity GA1950, 6.25 grams Affinity PL1840 G and 87.5 grams of LILAC (C14-22 hydrocarbon oil) are placed in a glass container. The container is placed on a hot plate or a heat jack, preferably set up as a closed system with Nitrogen filled on top of the space. Mixing with an overhead stirrer at a speed around 100-200 rpm, heat the batch up to 150° C. Hold the temperature at 150° C. and keep mixing for 1 hour and until all the solids are melted. When all solids are melted, turn off the heat, start cooling while mixing. When the temperature is around 80-90° C., cease mixing. Transfer the gel into a suitable sized glass jar, it will appear as an opaque paste. Similar process for Batch B.

Single polyolefin blends were tested, but either formed unstable gels or had poor aesthetics. Similarly, a molecular weight limit for solubility in a hydrocarbon medium and phase homogeneity was developed.

Example 2

Batch A and Batch B are tested by incorporating 5% polymer active of polyolefin oil blend in skin care lotion formulations (conventional lotion containing Water 53%, Glycerin 2%, Xanthan Gum 0.7% as the thickener, Cetearyl Alcohol (and) Ceteareth 20 3% as the emulsifier, Glyceryl Stearate 2% as the wax, Petrolatum 5% as the emollient, and Neolone PE 0.6% as the preservative). For comparison, a third skin care lotion was prepared using conventional DC 9045 silicone elasotmer gel as the sensory agent. Table 3 shows the in-vivo sensory results.

TABLE 3

|  | Lotion with Batch A | Lotion with Batch B | Comparative Lotion with DC 9045 |
| --- | --- | --- | --- |
| Spreading | −1 | 0 | 0 |
| Absorption | −2 | −2 | 0 |
| Oiliness | −1 | −1 | 0 |
| Waxiness | −1 | −1 | 0 |
| Tackiness | 0 | 0 | 0 |
| Smoothness | 0 | 0 | 0 |
| Softness | −1 | +1 | 0 |

The results show the inventive polyolefin blend oil gels compare favorably with the benchmark-DC 9045 on smoothness, softness, tackiness and spreading. The C14-22 hydrocarbon oil probably caused the slower absorption and more oiliness/waxiness feel, but is generally acceptable and likely can be routinely optimized. The stability of the inventive gels was favorable (unlike single component polyolefin oil gels).

The invention claimed is:

1. An oil gel skin care composition comprising:
   (a) a polyolefin blend comprising:
      at least one high density metallocene catalyzed polyolefin selected from the group consisting of polyethylene and ethylene/octene copolymers, wherein the high density polyolefin has a density above 0.90 g/cm$^3$, wherein the high density polyolefin is present in an amount of at least 6.25 weight %, based on the total weight of the composition; and
      at least one low density metallocene catalyzed polyolefin selected from ethylene/octene copolymers, wherein the low density polyolefin has a density equal to or below 0.90 g/cm$^3$, wherein the low density polyolefin is present in an amount of at least 4.17 weight %, based on the total weight of the composition;
      provided that the average melt index for the polyolefin blend is greater than 7; and (b) a cosmetically acceptable hydrocarbon oil, wherein the cosmetically acceptable hydrocarbon oil is $C_{14}$-$C_{22}$ hydrocarbon oil, wherein the hydrocarbon oil is present in an amount of at least 87 weight %, based on the total weight of the composition;

provided that the composition does not contain ethylene acrylic copolymer.

2. The oil gel skin care composition of claim 1, wherein the pH of the skin care composition is between 5 and 7.

3. The oil gel skin care composition of claim 1, wherein the polyolefin blend further comprises at least one of a silicone oil or silicone elastomer.

4. The oil gel skin care composition of claim 1, wherein the polyolefin blend further comprises an emollient.

5. The oil gel skin care composition of claim 1, wherein the ratio of at least one metallocene catalyzed polyolefin with a density above 0.90 g/cm$^3$ to the at least one metallocene catalyzed polyolefin with a density equal to or below 0.90 g/cm$^3$ is 1:1.

6. The oil gel skin care composition of claim 1, wherein the ratio of at least one metallocene catalyzed polyolefin with a density above 0.90 g/cm$^3$ to the at least one metallocene catalyzed polyolefin with a density equal to or below 0.90 g/cm$^3$ is 2:1.

7. The oil gel skin care composition of claim 1, provided that the average melt index for the polyolefin blend is greater than 8.

8. The oil gel skin care composition of claim 1, wherein provided that the average melt index for the polyolefin blend is greater than 8.5.

\* \* \* \* \*